US008540774B2

(12) United States Patent
Kueenzi et al.

(10) Patent No.: US 8,540,774 B2
(45) Date of Patent: Sep. 24, 2013

(54) LOW PROFILE INTERVERTEBRAL IMPLANT

(75) Inventors: Thomas Kueenzi, Downingtown, PA (US); Ryan Walsh, Douglassville, PA (US); Tom Pepe, Turnersville, NJ (US); Markus Hunziker, Aarau (CH); David Koch, Bubendorf (CH)

(73) Assignee: DePuy Synthes Products, LLC, Raynham, MA (US)

( * ) Notice: Subject to any disclaimer, the term of this patent is extended or adjusted under 35 U.S.C. 154(b) by 186 days.

(21) Appl. No.: 12/743,098

(22) PCT Filed: Nov. 5, 2008

(86) PCT No.: PCT/US2008/082473
§ 371 (c)(1),
(2), (4) Date: Aug. 25, 2010

(87) PCT Pub. No.: WO2009/064644
PCT Pub. Date: May 22, 2009

(65) Prior Publication Data
US 2010/0312346 A1   Dec. 9, 2010

Related U.S. Application Data

(60) Provisional application No. 60/988,661, filed on Nov. 16, 2007.

(51) Int. Cl.
*A61F 2/44* (2006.01)
(52) U.S. Cl.
USPC .................................. 623/17.16; 623/17.11
(58) Field of Classification Search
USPC ........................................ 623/17.11–17.16
See application file for complete search history.

(56) References Cited

U.S. PATENT DOCUMENTS

| 2,621,145 A | 12/1952 | Sano |
| 4,135,506 A | 1/1979 | Ulrich |

(Continued)

FOREIGN PATENT DOCUMENTS

| DE | 2821678 A | * 11/1979 |
| EP | 0517030 | 12/1992 |

(Continued)

OTHER PUBLICATIONS

International Search Report, mailed Mar. 20, 2009, for PCT International Application No. PCT/US08/82473, filed Nov. 5, 2008.

(Continued)

*Primary Examiner* — Andrew Yang
*Assistant Examiner* — Diana S Jones
(74) *Attorney, Agent, or Firm* — Stradley Ronon Stevens & Young, LLP

(57) ABSTRACT

The present invention is directed to a low profile intervertebral implant (10) for implantation in an intervertebral disc space (D) in-between adjacent vertebral bodies (V). The intervertebral implant includes a plate (40) preferably coupled to a spacer (20). The plate is preferably formed from a first material and the spacer is preferably formed from a second material, the first material being different from the second material. The plate is preferably sized and configured so that the plate does not extend beyond the perimeter of the spacer. In this manner, the plate preferably does not increase the height profile (hs) of the spacer and the plate may be implanted within the intervertebral disc space in conjunction with the spacer.

15 Claims, 10 Drawing Sheets

(56) References Cited

U.S. PATENT DOCUMENTS

| | | |
|---|---|---|
| 4,501,269 A | 2/1985 | Bagby |
| 4,512,038 A | 4/1985 | Alexander et al. |
| 4,627,853 A | 12/1986 | Campbell et al. |
| 4,678,470 A | 7/1987 | Nashef et al. |
| 4,717,115 A | 1/1988 | Schmitz et al. |
| 4,858,603 A | 8/1989 | Clemow et al. |
| 4,904,261 A | 2/1990 | Dove et al. |
| 4,936,851 A | 6/1990 | Fox et al. |
| 4,950,296 A | 8/1990 | McIntyre |
| 4,961,740 A | 10/1990 | Ray et al. |
| 4,994,084 A | 2/1991 | Brennan |
| 5,026,373 A | 6/1991 | Ray et al. |
| 5,053,049 A | 10/1991 | Campbell |
| 5,062,850 A | 11/1991 | MacMillan et al. |
| 5,084,051 A | 1/1992 | Tormala et al. |
| 5,112,354 A | 5/1992 | Sires |
| 5,139,424 A | 8/1992 | Yli-Urpo |
| 5,192,327 A | 3/1993 | Brantigan |
| 5,211,664 A | 5/1993 | Tepic et al. |
| 5,281,226 A | 1/1994 | Davydov et al. |
| 5,284,655 A | 2/1994 | Bogdansky et al. |
| 5,298,254 A | 3/1994 | Prewett et al. |
| 5,314,476 A | 5/1994 | Prewett et al. |
| 5,348,788 A | 9/1994 | White |
| 5,405,391 A | 4/1995 | Hednerson et al. |
| 5,423,817 A | 6/1995 | Lin |
| 5,439,684 A | 8/1995 | Prewett et al. |
| 5,458,638 A | 10/1995 | Kuslich et al. |
| 5,458,643 A | 10/1995 | Oka et al. |
| 5,489,308 A | 2/1996 | Kuslich et al. |
| 5,507,818 A | 4/1996 | McLaughlin |
| 5,514,180 A | 5/1996 | Heggeness et al. |
| 5,522,899 A | 6/1996 | Michelson |
| 5,534,030 A | 7/1996 | Navarro et al. |
| 5,549,679 A | 8/1996 | Kuslich |
| 5,554,191 A | 9/1996 | Lahille et al. |
| 5,556,430 A | 9/1996 | Gendler |
| 5,569,308 A | 10/1996 | Sottosanti |
| 5,571,190 A | 11/1996 | Ulrich et al. |
| 5,571,192 A | 11/1996 | Schönhöffer |
| 5,607,474 A | 3/1997 | Athanasiou et al. |
| 5,609,635 A | 3/1997 | Michelson |
| 5,609,636 A | 3/1997 | Kohrs et al. |
| 5,609,637 A | 3/1997 | Biedermann et al. |
| 5,676,699 A | 10/1997 | Gogolewski et al. |
| 5,683,394 A | 11/1997 | Rinner |
| 5,683,463 A | 11/1997 | Godefroy et al. |
| 5,702,449 A | 12/1997 | McKay |
| 5,702,451 A | 12/1997 | Biedermann et al. |
| 5,702,453 A | 12/1997 | Rabbe et al. |
| 5,702,455 A | 12/1997 | Saggar |
| 5,728,159 A | 3/1998 | Stroever et al. |
| 5,735,905 A | 4/1998 | Parr |
| 5,766,253 A | 6/1998 | Brosnahan, III |
| 5,776,194 A | 7/1998 | Mikol et al. |
| 5,776,197 A | 7/1998 | Rabbe et al. |
| 5,776,198 A | 7/1998 | Rabbe et al. |
| 5,776,199 A | 7/1998 | Michelson |
| 5,782,915 A | 7/1998 | Stone |
| 5,785,710 A | 7/1998 | Michelson |
| 5,800,433 A | 9/1998 | Benzel et al. |
| 5,865,849 A | 2/1999 | Stone |
| 5,876,452 A | 3/1999 | Athanasiou et al. |
| 5,885,299 A | 3/1999 | Winslow et al. |
| 5,888,222 A | 3/1999 | Coates et al. |
| 5,888,223 A | 3/1999 | Bray, Jr. |
| 5,888,224 A | 3/1999 | Beckers et al. |
| 5,888,227 A | 3/1999 | Cottle |
| 5,895,426 A | 4/1999 | Scarborough et al. |
| 5,899,939 A | 5/1999 | Boyce et al. |
| 5,902,338 A | 5/1999 | Stone |
| 5,904,719 A | 5/1999 | Errico et al. |
| 5,910,315 A | 6/1999 | Stevenson et al. |
| 5,922,027 A | 7/1999 | Stone |
| 5,944,755 A | 8/1999 | Stone |
| 5,958,314 A | 9/1999 | Draenert |
| 5,968,098 A | 10/1999 | Winslow |
| 5,972,368 A | 10/1999 | McKay |
| 5,976,187 A | 11/1999 | Richelsoph |
| 5,980,522 A * | 11/1999 | Koros et al. ............... 623/17.11 |
| 5,981,828 A | 11/1999 | Nelson et al. |
| 5,984,967 A | 11/1999 | Zdeblick et al. |
| 5,989,289 A | 11/1999 | Coates et al. |
| 6,013,853 A | 1/2000 | Athanasiou et al. |
| 6,025,538 A | 2/2000 | Yaccarino, III |
| 6,033,405 A | 3/2000 | Winslow et al. |
| 6,033,438 A | 3/2000 | Bianchi et al. |
| 6,039,762 A | 3/2000 | McKay |
| 6,045,579 A | 4/2000 | Hochshuler et al. |
| 6,045,580 A | 4/2000 | Scarborough et al. |
| 6,066,175 A | 5/2000 | Henderson et al. |
| 6,080,158 A | 6/2000 | Lin |
| 6,080,193 A | 6/2000 | Hochshuler et al. |
| 6,090,998 A | 7/2000 | Grooms et al. |
| 6,096,081 A | 8/2000 | Grivas et al. |
| 6,110,482 A | 8/2000 | Khouri et al. |
| 6,123,731 A | 9/2000 | Boyce et al. |
| 6,129,763 A | 10/2000 | Chauvin et al. |
| 6,143,030 A | 11/2000 | Schroder |
| 6,143,033 A | 11/2000 | Paul et al. |
| 6,156,070 A | 12/2000 | Incavo et al. |
| 6,193,756 B1 | 2/2001 | Studer et al. |
| 6,200,347 B1 | 3/2001 | Anderson et al. |
| 6,206,922 B1 | 3/2001 | Zdeblick et al. |
| 6,231,610 B1 | 5/2001 | Geisler |
| 6,235,059 B1 | 5/2001 | Benezech et al. |
| 6,241,769 B1 | 6/2001 | Nicholson et al. |
| 6,245,108 B1 | 6/2001 | Biscup |
| 6,258,125 B1 | 7/2001 | Paul et al. |
| 6,261,586 B1 | 7/2001 | McKay |
| 6,264,695 B1 | 7/2001 | Stoy |
| 6,270,528 B1 | 8/2001 | McKay |
| 6,342,074 B1 * | 1/2002 | Simpson ............... 623/17.11 |
| 6,364,880 B1 | 4/2002 | Michelson |
| 6,371,988 B1 | 4/2002 | Pafford et al. |
| 6,371,989 B1 | 4/2002 | Chauvin et al. |
| 6,375,681 B1 | 4/2002 | Truscott |
| 6,423,063 B1 | 7/2002 | Bonutti |
| 6,432,106 B1 | 8/2002 | Fraser |
| 6,458,158 B1 | 10/2002 | Anderson et al. |
| 6,468,311 B2 | 10/2002 | Boyd et al. |
| 6,569,201 B2 | 5/2003 | Moumene et al. |
| 6,602,291 B1 | 8/2003 | Ray et al. |
| 6,638,310 B2 | 10/2003 | Lin et al. |
| 6,682,561 B2 | 1/2004 | Songer et al. |
| 6,761,739 B2 | 7/2004 | Shepard |
| 6,863,673 B2 * | 3/2005 | Gerbec et al. ............... 606/99 |
| 6,923,756 B2 | 8/2005 | Sudakov et al. |
| 6,972,019 B2 | 12/2005 | Michelson |
| 6,984,234 B2 * | 1/2006 | Bray ............... 606/279 |
| 7,112,222 B2 | 9/2006 | Fraser et al. |
| 7,163,561 B2 | 1/2007 | Michelson |
| 7,172,627 B2 | 2/2007 | Fiere et al. |
| 7,232,464 B2 | 6/2007 | Mathieu et al. |
| 7,534,265 B1 | 5/2009 | Boyd et al. |
| 7,618,456 B2 | 11/2009 | Mathieu et al. |
| 7,637,951 B2 | 12/2009 | Michelson |
| 7,655,042 B2 | 2/2010 | Foley et al. |
| 7,862,616 B2 | 1/2011 | Lechmann et al. |
| 2001/0001129 A1 | 5/2001 | McKay et al. |
| 2001/0005796 A1 | 6/2001 | Zdeblick et al. |
| 2001/0010021 A1 | 7/2001 | Boyd et al. |
| 2001/0016777 A1 | 8/2001 | Biscup |
| 2001/0020186 A1 | 9/2001 | Boyce et al. |
| 2001/0031254 A1 | 10/2001 | Bianchi et al. |
| 2001/0039456 A1 | 11/2001 | Boyer, II et al. |
| 2001/0041941 A1 | 11/2001 | Boyer, II et al. |
| 2002/0010511 A1 | 1/2002 | Michelson |
| 2002/0022843 A1 | 2/2002 | Michelson |
| 2002/0029084 A1 | 3/2002 | Paul et al. |
| 2002/0082597 A1 | 6/2002 | Fraser |
| 2002/0082603 A1 | 6/2002 | Dixon et al. |
| 2002/0091447 A1 | 7/2002 | Shimp et al. |
| 2002/0099376 A1 | 7/2002 | Michelson |

| | | | |
|---|---|---|---|
| 2002/0106393 A1 | 8/2002 | Bianchi et al. | |
| 2002/0111680 A1 | 8/2002 | Michelson | |
| 2002/0147450 A1 | 10/2002 | LeHuec et al. | |
| 2002/0169508 A1 | 11/2002 | Songer et al. | |
| 2003/0078668 A1 | 4/2003 | Michelson | |
| 2003/0125739 A1 | 7/2003 | Bagga et al. | |
| 2004/0126407 A1 | 7/2004 | Falahee | |
| 2004/0210310 A1 | 10/2004 | Trieu | |
| 2004/0210314 A1 | 10/2004 | Michelson | |
| 2004/0249377 A1 | 12/2004 | Kaes et al. | |
| 2005/0033433 A1 | 2/2005 | Michelson | |
| 2005/0085913 A1 | 4/2005 | Fraser et al. | |
| 2005/0101960 A1 | 5/2005 | Fiere et al. | |
| 2005/0171606 A1 | 8/2005 | Michelson | |
| 2005/0171607 A1 | 8/2005 | Michelson | |
| 2005/0261767 A1 | 11/2005 | Anderson et al. | |
| 2006/0030851 A1 | 2/2006 | Bray et al. | |
| 2006/0085071 A1* | 4/2006 | Lechmann et al. | 623/17.11 |
| 2006/0229725 A1 | 10/2006 | Lechmann et al. | |
| 2008/0161925 A1 | 7/2008 | Brittan et al. | |
| 2009/0210064 A1 | 8/2009 | Lechmann et al. | |

FOREIGN PATENT DOCUMENTS

| | | |
|---|---|---|
| WO | WO 97/20526 | 6/1997 |
| WO | WO 97/23175 | 7/1997 |
| WO | WO 99/38463 | 8/1999 |
| WO | 00/25706 | 5/2000 |
| WO | WO 00/66045 | 11/2000 |
| WO | WO 01/56497 | 8/2001 |
| WO | WO 2007/098288 | 2/2007 |

OTHER PUBLICATIONS

Written Opinion, mailed Mar. 20, 2009, for PCT International Application No. PCT/US08/82473, filed Nov. 5, 2008.

Bray, R.S., M.D., "InterPlate Spine Fusion Device: Subsidence Control Without Stress Shielding", Orthopaedic Product News, Sep./Oct. 2006, pp. 22-25.

Synthes Spine, "SynFix-LR System. Instruments and implants for stand-alone anterior lumbar interbody fusion (ALIF)", Technique Guide (2008), pp. 2-40, published by Synthes Spine (USA).

Synthes Spine, "Zero-P Instruments and Implants. Zero-profile anterior cervical interbody fusion (ACIF) device", Technique Guide (2008), pp. 2-32, published by Synthes Spine (USA).

* cited by examiner

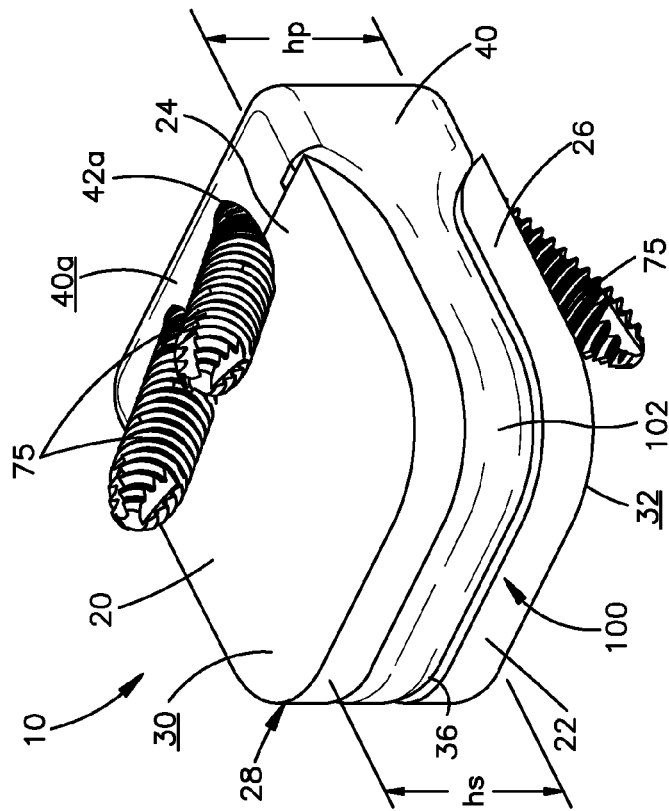
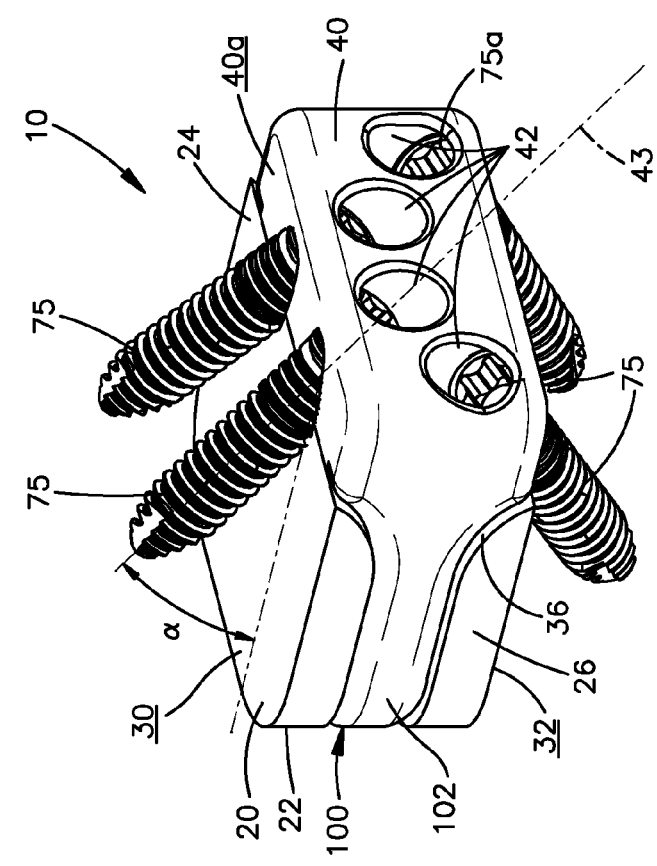
Fig.1A
Fig.1B

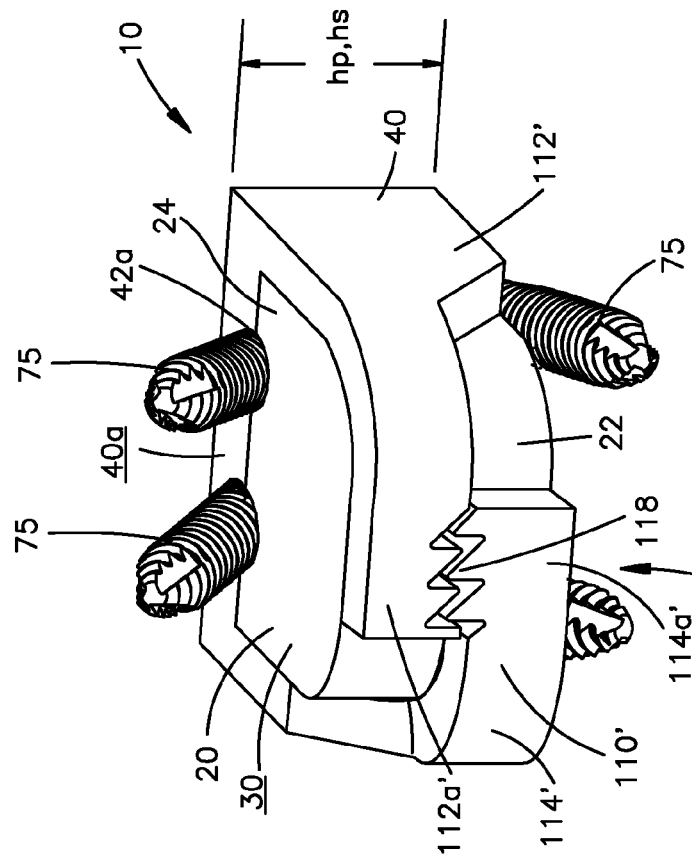
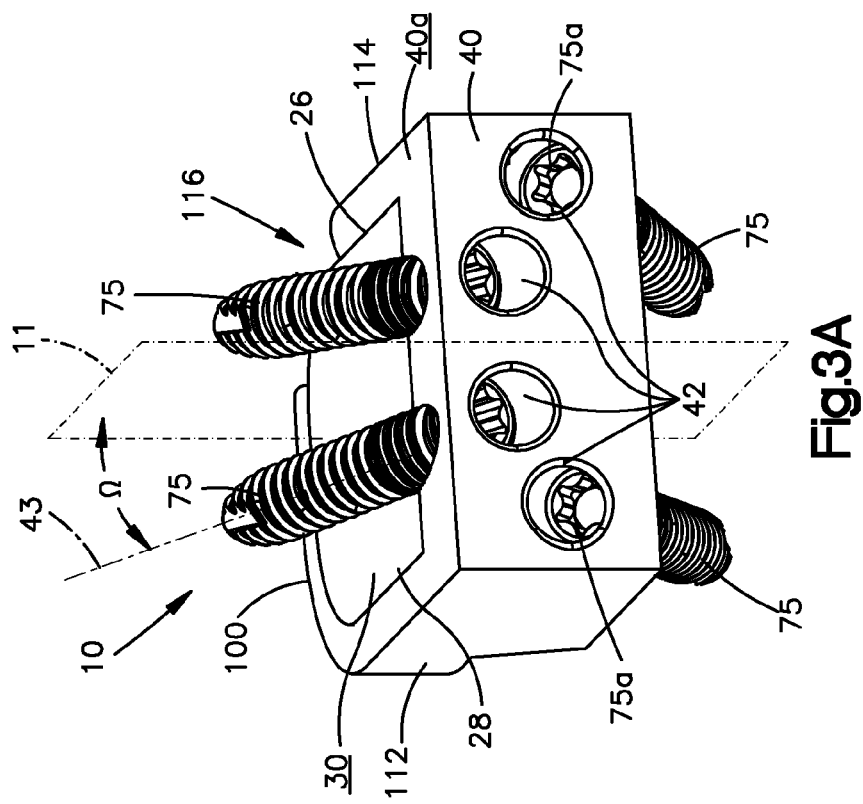

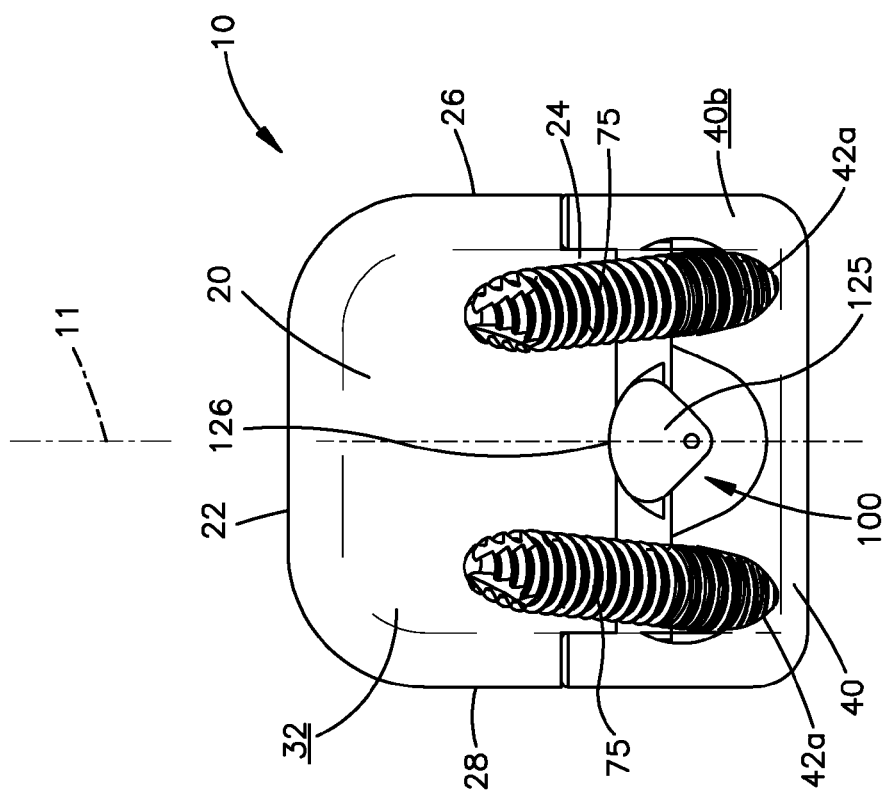
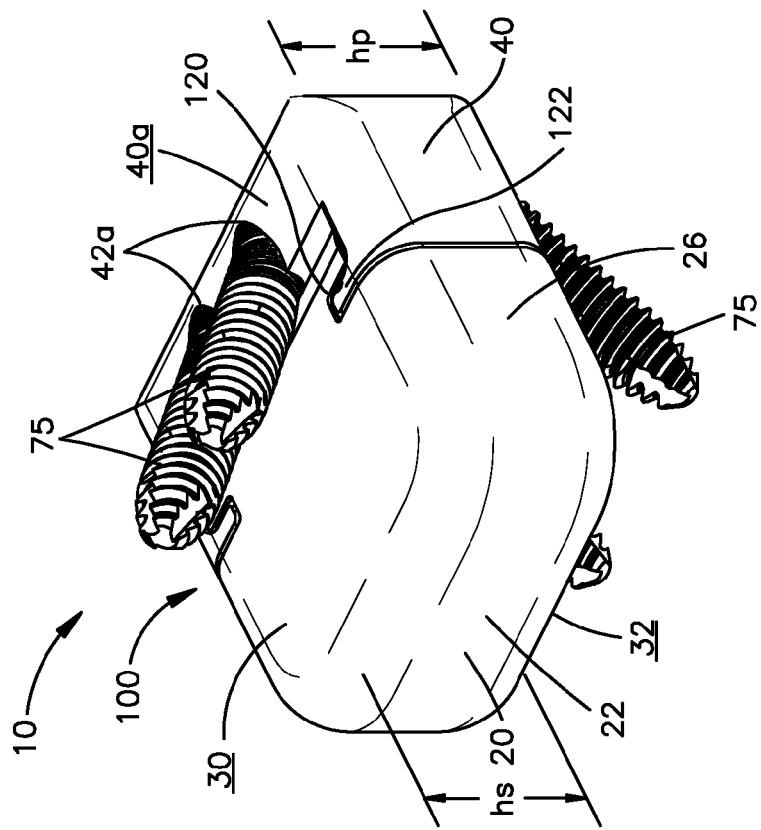

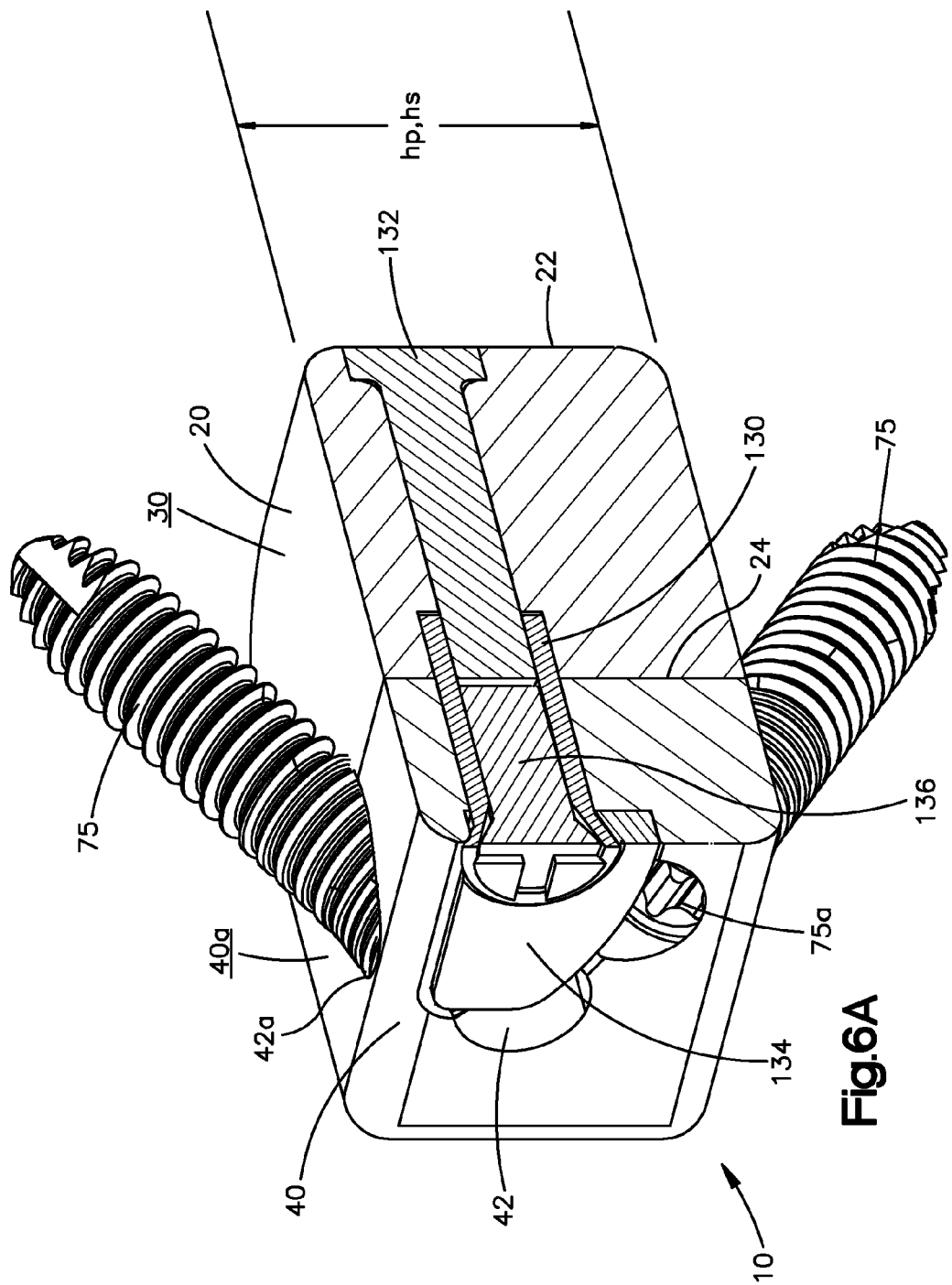

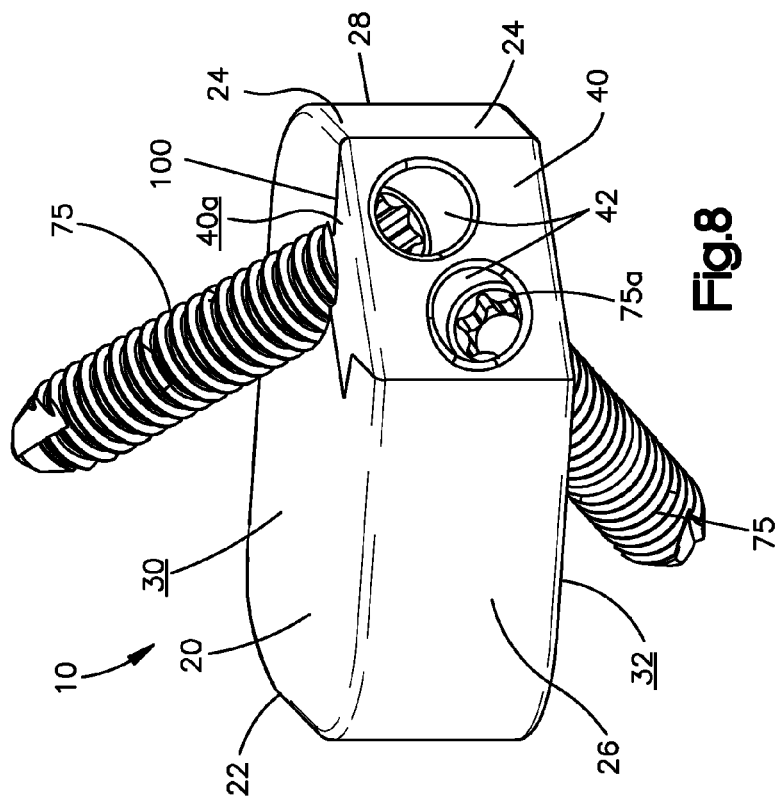
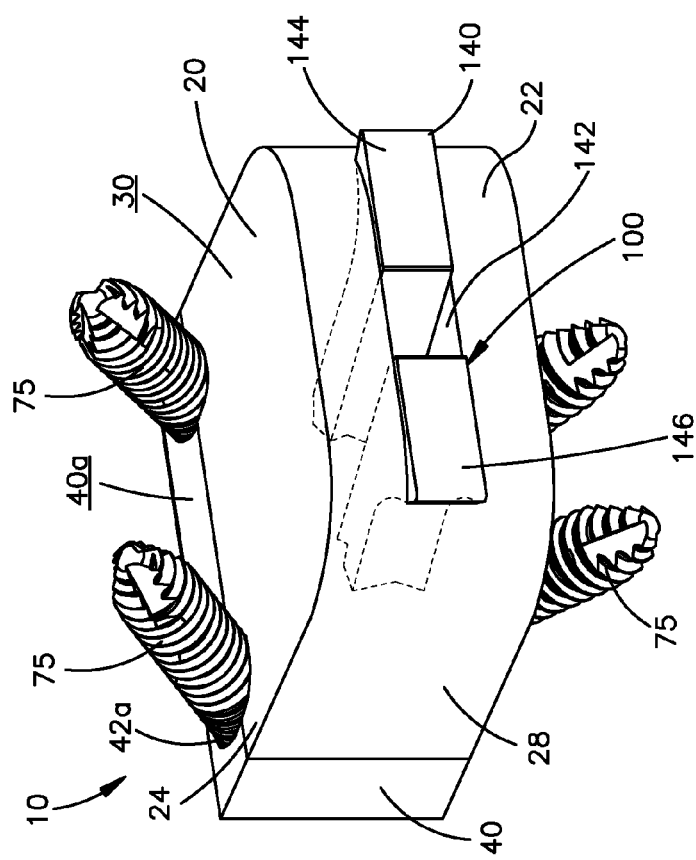

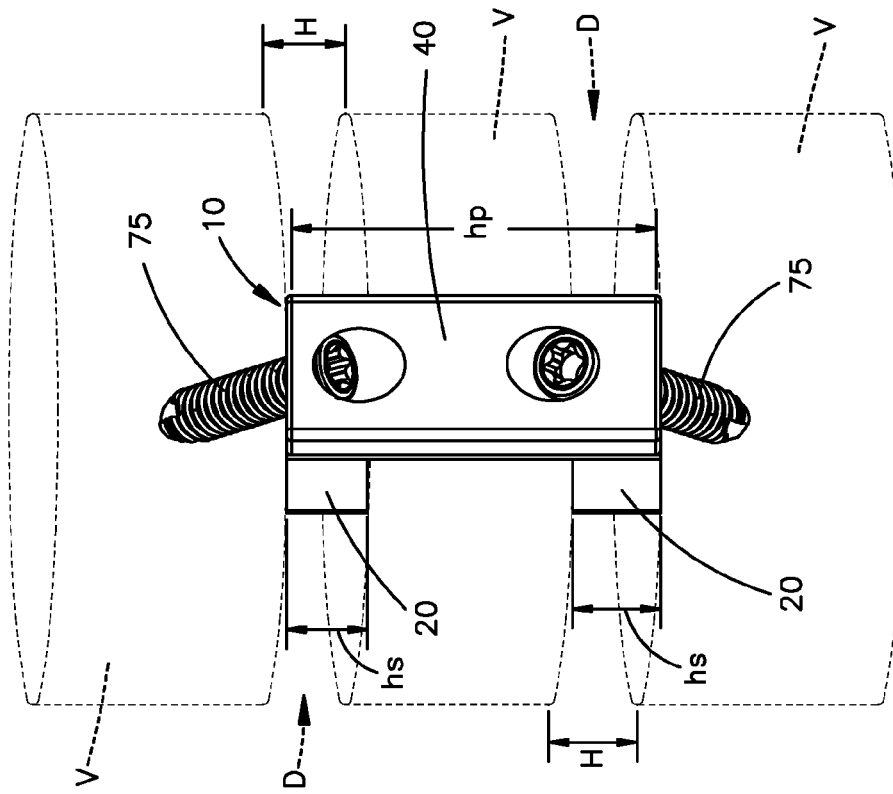
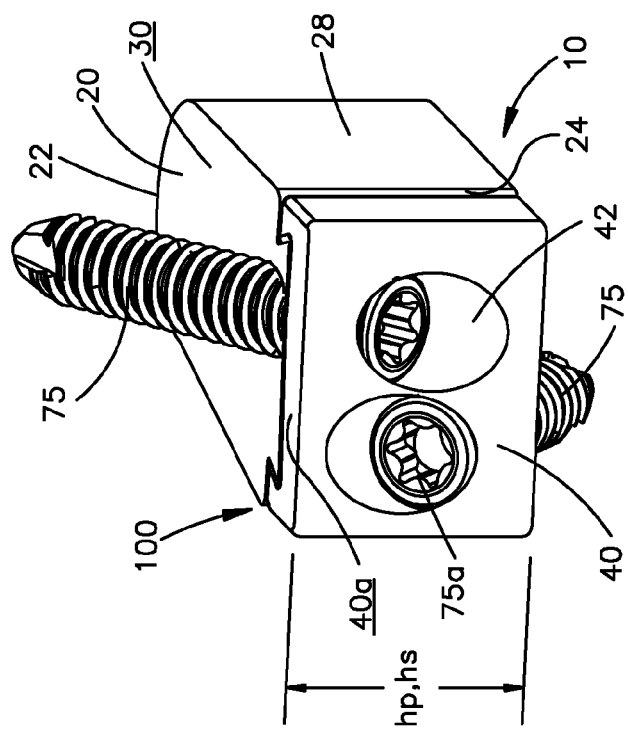
Fig.9
Fig.10

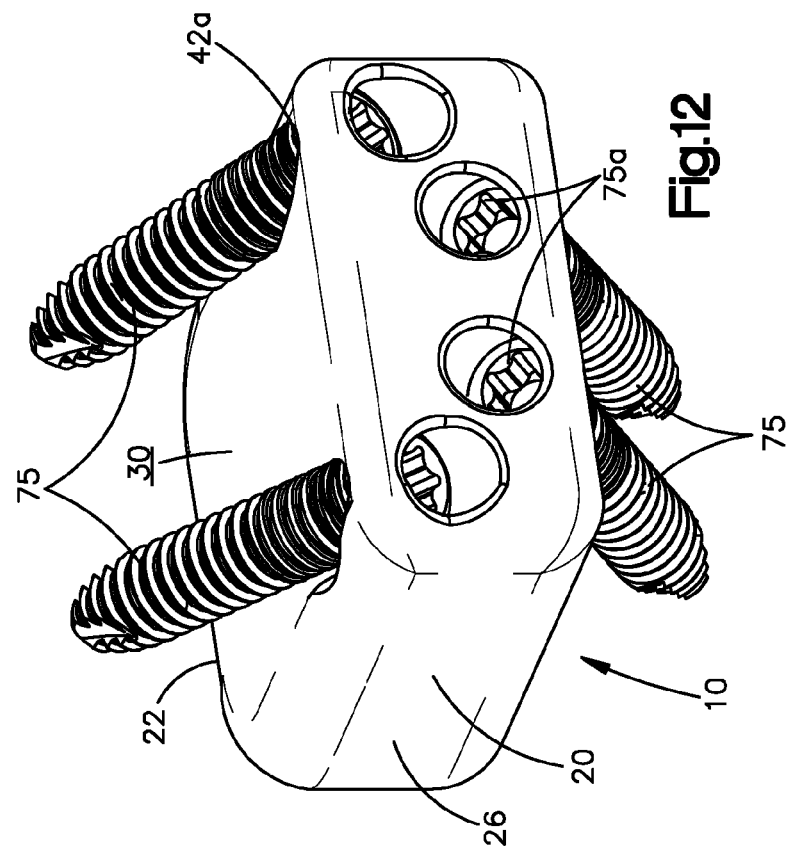
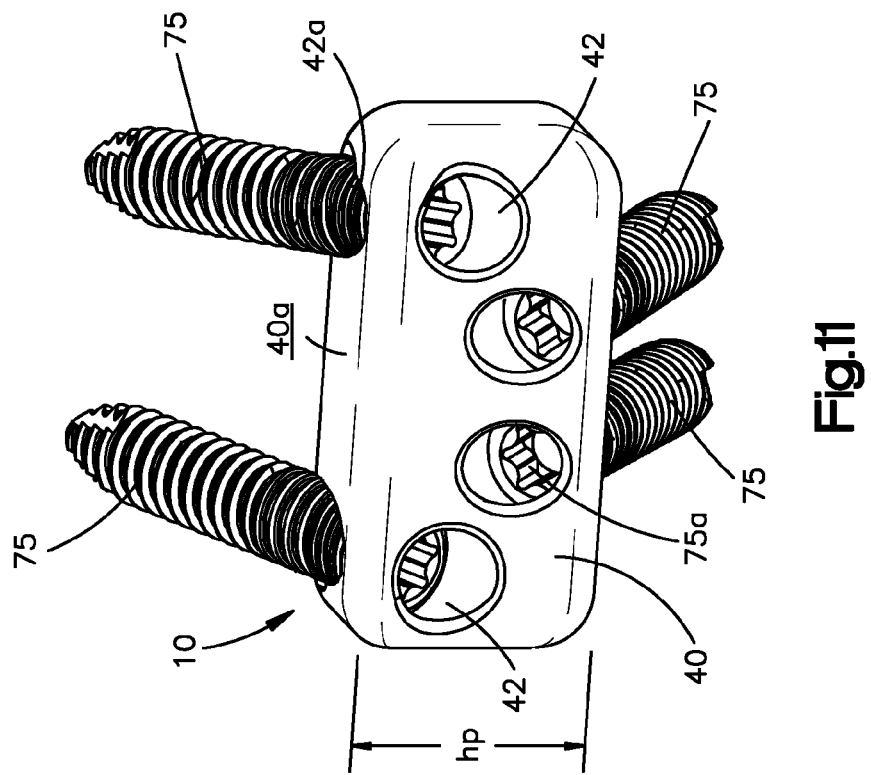

LOW PROFILE INTERVERTEBRAL IMPLANT

CROSS REFERENCE TO RELATED APPLICATIONS

This application claims priority to U.S. Provisional Patent Application Ser. No. 60/988,661, filed Nov. 16, 2007, the content of which is hereby incorporated by reference in its entirety.

FIELD OF THE INVENTION

The present invention relates to an intervertebral implant. More specifically, the preferred embodiment of the present invention relates to a low profile fusion intervertebral implant for implantation into the intervertebral disc space between adjacent vertebral bodies.

BACKGROUND OF THE INVENTION

Millions of people suffer from back pain. In some instances, in order to relieve back pain and/or to stabilize the spinal structure, it becomes necessary to fuse adjacent vertebral bodies at one or more levels. One known method for fusing adjacent vertebral bodies is to implant one or more intervertebral implants into the affected disc space.

SUMMARY OF THE INVENTION

A preferred embodiment of the present invention is directed to a low profile intervertebral implant for implantation in an intervertebral disc space between adjacent vertebral bodies. The intervertebral implant includes a plate preferably coupled to a spacer. The plate is preferably sized and configured so that the plate does not extend beyond the perimeter of the spacer. In this manner, the plate preferably does not increase the height profile of the spacer and the plate may be implanted within the intervertebral disc space in conjunction with the spacer.

In another aspect of the preferred embodiment of the intervertebral implant, the plate is coupled to the spacer by one or more arms extending from the plate. The arms are sized and configured to substantially surround and receive the spacer so that the spacer is securely coupled to the plate. The one or more arms may be a circumferential arm that extends from the plate and which completely wraps around the spacer. The circumferential arm may be sized and configured to shrink as a result of temperature variation. Alternatively, the arms may be a plurality of deformable arms sized and configured to receive the spacer. The arms are preferably deformable to substantially surround and compress against the spacer to secure the spacer to the arms. Alternatively, the one or more arms may be selectively interconnected with one another so that the first and second arms may be placed around the spacer and then tightened to operatively couple the spacer to the plate.

BRIEF DESCRIPTION OF THE DRAWINGS

The foregoing summary, as well as the following detailed description of the preferred embodiments of the application, will be better understood when read in conjunction with the appended drawings. For the purposes of illustrating the preferred intervertebral implants of the present application, there is shown in the drawings preferred embodiments. It should be understood, however, that the application is not limited to the precise arrangements and instrumentalities shown. In the drawings:

FIG. 1A illustrates a rear perspective view of an intervertebral implant in accordance with a first preferred embodiment of the present invention;

FIG. 1B illustrates a top perspective view of the intervertebral implant shown in FIG. 1A;

FIG. 3A illustrates a rear perspective view of an intervertebral implant in accordance with a third preferred embodiment of the present invention;

FIG. 3B illustrates a front perspective view of the intervertebral implant shown in FIG. 3A;

FIG. 4A illustrates a top perspective view of an intervertebral implant in accordance with a fourth preferred embodiment of the present invention;

FIG. 4B illustrates a bottom plan view of the intervertebral implant shown in FIG. 4A;

FIG. 6A illustrates a cross-sectional view of the intervertebral implant shown in FIG. 6, taken along line 6a-6a in FIG. 6 with the intervertebral implant in an assembled configuration;

FIG. 7 illustrates a front perspective view of an intervertebral implant in accordance with a seventh preferred embodiment of the present invention;

FIG. 8 illustrates a rear perspective view of an intervertebral implant in accordance with an eighth preferred embodiment of the present invention;

FIG. 9 illustrates a rear perspective view of an intervertebral implant in accordance with an ninth preferred embodiment of the present invention;

FIG. 10 illustrates a rear elevational view of an intervertebral implant in accordance with a tenth preferred embodiment of the present invention, wherein the intervertebral implant is mounted to a spine;

FIG. 11 illustrates a rear perspective view of an intervertebral implant in accordance with an eleventh preferred embodiment of the present invention; and FIG. 12 illustrates a rear perspective view of an intervertebral implant in accordance with a twelfth preferred embodiment of the present invention.

DETAILED DESCRIPTION OF THE INVENTION

Figure 2:
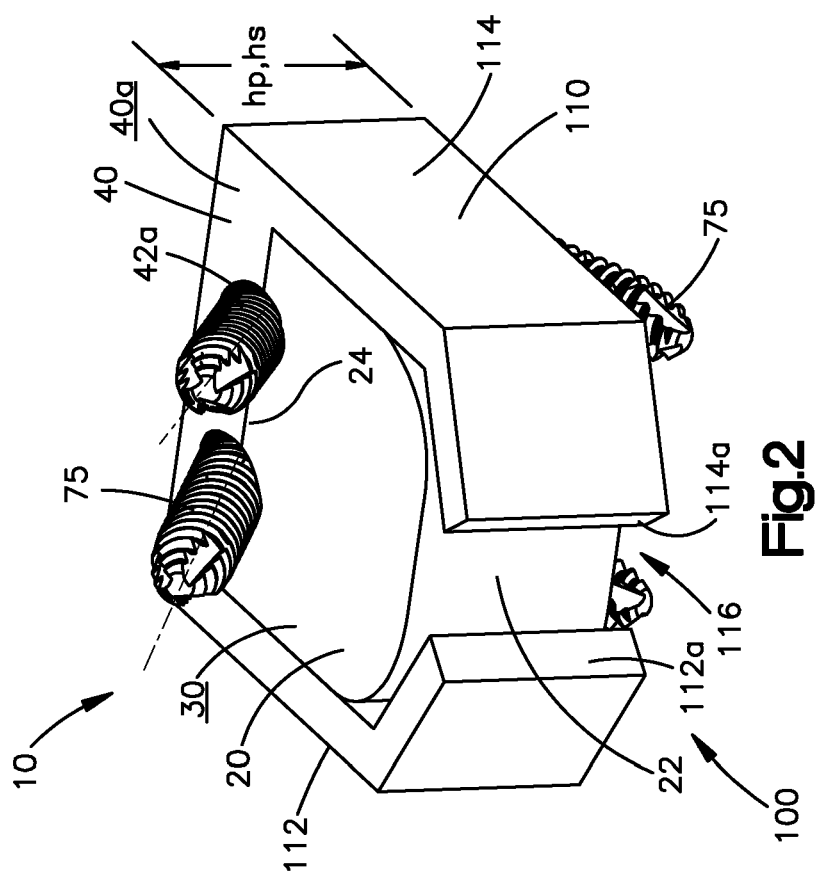
FIG. 2 illustrates a front perspective view of an intervertebral implant in accordance with a second preferred embodiment of the present invention.

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Referring to FIGS. 1A-12, certain exemplary embodiments of the invention will now be described with reference to the drawings. In general, such embodiments relate to a low profile intervertebral implant 10. It should be understood that while the various embodiments of the intervertebral implant 10 will be described in connection with spinal surgery, those skilled in the art will appreciate that the intervertebral implant 10 as well as the components thereof may be used for implantation into other parts of the body. The same reference numerals will be utilized throughout the application to describe similar or the same components of each of the twelve preferred embodiments of the preferred intervertebral implants described herein and the descriptions will focus on the specific features of the individual embodiments that distinguish the particular embodiment from the others.

Generally speaking, the various embodiments of the intervertebral implant 10 are sized and configured to be implanted between adjacent vertebral bodies V. The intervertebral implants 10 may be sized and configured to replace all or substantially all of an intervertebral disc space D between adjacent vertebral bodies V or only part of the intervertebral disc space D. In addition, the preferred intervertebral implants 10 may be configures to replace an entire vertebral body V and related disc spaces D or multiple disc spaces D in a patient's spine, as is apparent to one having ordinary skill in the art.

The intervertebral implants 10 of each of the preferred embodiments preferably include a plate 40 and a spacer 20. The spacer 20 may include a first insertion end portion 22 (e.g., front end), a second end portion 24 (e.g., rear end) opposite the first insertion end portion 22, a first lateral end 26, a second lateral end 28, an upper surface 30, and a lower surface 32. The spacer 20 is preferably configured and dimensioned for implantation into the intervertebral disc space D between adjacent vertebral bodies V. The spacer 20 is preferably sized and configured to maintain and/or restore a desired intervertebral disc height H between the adjacent vertebral bodies V.

The plate 40 is preferably mounted to the second end portion 24 of the spacer 20 and preferably does not extend beyond the perimeter of the spacer 20. That is, a plate height $h_p$ of the plate 40 is preferably no more than a spacer height $h_s$ of the spacer 20 at the second end 24 so that the plate 40 does not increase the height profile of the spacer 20. In this manner, the intervertebral implant 10 has a low profile. Additionally, in this manner, the plate 40 may be entirely implanted into the intervertebral disc space D between the adjacent vertebral bodies V such that the plate 40 does not extend beyond an edge of the disc space D.

The upper and lower surfaces 30, 32 of the spacer 20 may include a series of teeth, one or more keels, or other similar projections (not shown) to aid in securing the intervertebral implant 10 to the endplates of the adjacent vertebral bodies V. Alternatively or in addition, the spacer 20 may include one or more windows or channels (not shown) designed to receive bone graft material. For example, the spacer 20 may include one or more vertical windows or channels (not shown) extending through the spacer 20 from the upper surface 30 to the lower surface 32 for insertion of bone graft material such that bone growth is promoted through the vertical windows or channels following implantation of the intervertebral implant 10. Alternatively or in addition, the spacer 20 may have one or more horizontal windows or channels (not shown) extending through the spacer 20 from the first lateral end 26 to the second lateral end 28 for receiving bone graft material.

The upper and lower surfaces 30, 32 of the spacer 20 may include a curved or a tapered surface to help provide the proper shape to the spine or to orient the endplates of the adjacent vertebral bodies V in a desired manner. The particular surface shape and curvature or taper in the anterior-posterior direction as well as between the first and second lateral ends 26, 28 will depend upon the location the implant 10 is intended to be implanted and/or surgeon preferences.

The intervertebral implant 10 may be constructed of any suitable material or combination of materials including, but not limited to polymer (e.g. PEEK), titanium, titanium alloy, stainless steel, Nitinol, tantalum nitride (TaN), allograft bone, bioresorbable material, magnesium, composites, synthetic bone-welding polymers, etc. The plate 40 may be formed of a different material than the spacer 20. For example, the plate 40 may be formed of a metallic material such as, for example, a titanium or a titanium alloy, and the spacer 20 may be formed of a non-metallic material such as, for example, an allograft, a polymer, a bioresorbable material, a ceramic, etc. Alternatively, the plate 40 and the spacer 20 may be formed from the same material. For example, the plate 40 and the spacer 20 may both be constructed of tantalum nitride (TaN).

The plate 40 preferably includes one or more through holes 42 for receiving fasteners 75 such as, for example, one or more bone screws 75, for securing the intervertebral implant 10 to the adjacent vertebral bodies V. The plate 40 may include any number of through holes 42 arranged in any number of combinations. For example, the plate 40 may include two, three, four or more through holes 42 for receiving, preferably, an equal number of bone screws 75. Moreover, the through holes 42 may alternate with one another with one through hole 42 being angled up and the next through hole 42 being angled down (FIGS. 8 and 9), or the through holes 42 on the outside may be angled up while the through holes 42 on the inside may be angled down (FIGS. 5-7, 11 and 12), etc.

The plate 40 of the preferred embodiments includes at least two through holes 42 configured to receive two fasteners 75 for securing the intervertebral implant 10 to the adjacent vertebral bodies V. The at least two through holes 42 preferably diverge so that at least one fastener 75 is secured into the upper vertebral body V while at least one other fastener 75 is secured into the lower vertebral body V so that opposing forces act on the plate 40 and/or vertebral bodies V. Alternatively, the plate 40 may include three through holes 42 configured to receive three fasteners 75. One fastener 75 may penetrate the upper vertebral body V and two fasteners 75 may penetrate the lower vertebral body V, or vice versa. Alternatively, the plate 40 may include four or more through holes 42 configured to receive four or more fasteners 75. In such a configuration, two inner fasteners 75 may penetrate the upper vertebral body V while two outer fasteners 75 may penetrate the lower vertebral body V, or vice versa, or some combination thereof.

The through holes 42 each include a hole axis 43 such that one of the holes 42 exit through the upper surface of the intervertebral implant 10, possibly through the upper surface 30, for engaging the upper vertebral body V while another of the holes 42 exit through the lower surface of the intervertebral implant 10, possibly through the lower surface 32 for engaging the lower vertebral body V. The fastener 75 that extends through the hole 42, preferably along the hole axis 43 forms a fastener angle α with respect to the upper and lower surfaces 30, 32 of the spacer 20 wherein fastener angle α may be in the range between twenty degrees (20°) and fifty degrees (50°), and most preferably between thirty degrees (30°) and forty-five degrees (45°). The fastener angle α may be the same for all of the holes 42 or may be different for each of the holes 42.

The though holes 42 formed in the plate 40 preferably are directed outwardly from the center of the intervertebral implant 10, preferably at a lateral fastener angle Ω. Thus, the through holes 42 preferably extend laterally outward from a center plane 11 of the intervertebral implant 10 at the lateral fastener angle Ω. The lateral fastener angle Ω may be the same for all holes 42 or may be different for each hole 42.

Exit openings 42a of the through holes 42 may be formed in the plate 40 or in the spacer 20. The through holes 42 may also include one or more threads (not shown) for threadably engaging threads formed on a head portion 75a of the bone screw 75 in order to secure the bone screws 75 to the plate 40 and to generally lock the position of the bone screws 75 relative to the plate 40 and/or spacer 20.

The intervertebral implant 10 of the preferred embodiments also preferably includes a coupling mechanism 100 for securing the plate 40 to the spacer 20. Generally speaking, the spacer 20 and the plate 40 are coupled together by the coupling mechanism 100 prior to being implanted into the disc space D. However, in certain embodiments, the intervertebral implant 10 may be configured so that the plate 40 may be coupled to the spacer 20 after one of the spacer 20 and plate 40 have been implanted into the intervertebral disc space. Once coupled, the spacer 20 and plate 40 preferably form a solid implant. The coupling mechanism 100 may be any of the coupling mechanisms 100 described herein or their structural equivalents.

Referring to a first preferred embodiment of the intervertebral implant 10 shown in FIGS. 1A and 1B, the coupling mechanism 100 may be in the form of a solid, circumferential arm 102 that extends from the plate 40. The circumferential arm 102 is preferably sized and configured to wrap around and/or to receive the spacer 20 therein. Preferably, the spacer 20 includes a recess 36 formed on the outer surfaces thereof for receiving at least a portion of the circumferential arm 102.

The circumferential arm 102 may be made from a material that deforms or shrinks as a result of being heated or cooled such as, for example, Nitinol or any other suitable material that deforms as a result of temperature variation. In this manner, the plate 40 may be fixed to the spacer 20 by heating or cooling the plate 40, thereby causing the arm 102 of the plate 40 to shrink, which in turn causes the arm 102 to circumferentially engage the spacer 20. This first preferred embodiment of the is particularly useful since it enables relatively loose tolerances during manufacturing of the spacer 20.

Referring to a second preferred embodiment of the intervertebral implant 10 shown in FIG. 2, the coupling mechanism 100 may be in the form of a split ring 110. That is, the plate 40 may include a pair of arms 112, 114 extending therefrom, wherein the arms 112, 114 are sized and configured to substantially surround the outer circumference of the spacer 20 in order to couple the spacer 20 to the plate 40. The arms 112, 114 are preferably configured so as to be deformable around the spacer 20. That is, the arms 112, 114 are preferably able to deform so that the arms 112, 114 can wrap around and/or squeeze the spacer 20. The intervertebral implant 10 of the second preferred embodiment is not limited to having the pair of arms 112, 114 and may include nearly any number of arms extending from the plate 40 that are deformable to engage and secure the spacer 20 relative to the plate 40.

As best shown in FIG. 2, the split ring 110 may be include an open gap 116 proximate the first insertion end portion 22 of the implant 10 that defines terminal ends 112a, 114a of the arms 112, 114. The end portions of the arms 112, 114 proximate the terminal ends 112a, 114a are preferably deformable to permit manual clamping of the spacer 20 with the arms 112, 114 to secure the spacer 20 to the plate 40. The gap 116 is not limited to being positioned generally along a midline of the spacer 20 opposite the plate 40 and may be located at nearly any position relative to the plate 40 that permits the arms 112, 114 to deform and clamp or otherwise secure the spacer 20 to the plate 40. For example, the gap 116 may be positioned proximate a corner of the preferred spacer 20 proximate an intersection of the first insertion end portion 22 and one of the first and second lateral ends 26, 28

Referring to FIGS. 3A and 3B, in a third preferred embodiment of the intervertebral implant 10, the split ring 110' may be sized and configured so that the arms 112', 114' may be interconnected to one another at their terminal ends 112a', 114a' so that, in use, the split ring 110' may be placed around the spacer 20 and then tightened to operatively couple the plate 40 to the spacer 20. The interconnected arms 112', 114' of the split ring 110' of the third preferred embodiment may be tighten by any means including but not limited to a ratcheting locking mechanism 118, a hose clamp design, etc. Incorporation of the split ring 110' of the third preferred embodiment enables the plate 40 to accommodate spacers 20 of variable dimensions and compositions. Furthermore, incorporation of the split ring 110' of the third preferred embodiment may enable the intervertebral implant 10 to be assembled in situ. Other, alternate designs of the plate 40 that allow for the coupling of the plate 40 around the spacer 20 are envisioned. Alternatively, incorporation of the split ring 110' of the third preferred embodiment may enable the surgeon to incorporate bone packing material as opposed to a pre-formed spacer 20 as described herein and as would be apparent to one having ordinary skill in the art.

Referring to the fourth preferred embodiment of the intervertebral implant 10 shown in FIGS. 4A and 4B, the coupling mechanism 100 may be in the form of a recess 120 preferably extending from the upper surface 30 to the lower surface 32 of the spacer 20 to engage a projection 122 formed on and extending from the plate 40 in an assembled configuration. The recess 120 may be formed in the first and second lateral ends 26, 28 of the spacer 20, in only one of the first and second lateral ends 26, 28, centrally within the spacer 20 or otherwise formed for engagement by the projection 122. For example, as shown, the coupling mechanism 100 of the fourth preferred embodiment is in the form of a dovetail joint, wherein the recess 120 is comprised of recesses 120 extending from the top surface 30 toward the bottom surface 32 proximate the second end 24 and the first and second lateral ends 26, 28, respectively. In this fourth preferred embodiment, the coupling mechanism 100 preferably enables the plate 40 to unidirectionally, slidably engage the spacer 20 by sliding the projection 122 into the recess 120, wherein the projection 122 and recess 120 are formed to prevent the spacer 20 from being engaged with the plate 40 unless the spacer 20 is aligned with the plate 40 and slides along a unitary engagement direction. Alternatively, the projection 122 formed on the plate 40 may be sized and configured to flex across the spacer 20 until the projections 122 substantially fit inside the recesses 120 thereby coupling the spacer 20 to the plate 40 via a press-fit arrangement. It should be appreciated that the locations of the projections 122 and the recesses 120 may be reversed so that the spacer 20 includes the projections and the plate 40 includes the recesses, respectively. In addition, the projections 122 and recesses 120 are preferably sized to align the spacer 20 with the plate 40 such that the top surface 30 of the spacer 20 is generally coplanar with a top surface 40a of the plate 40 and a bottom surface 32 of the spacer 20 is generally coplanar or aligned with a bottom surface 40b of the plate 40 in the assembled configuration. Specifically, the projections 122 and the recesses 120 may be tapered to promote the unitary insertion of the spacer 20 into engagement with the plate 40 and alignment of the top and bottom surfaces 40a, 40b of the plate 40 with the top and bottom surfaces 30, 32 of the spacer 20 in the assembled configuration.

In addition, the coupling mechanism 100 of the fourth preferred embodiment may include one or more rotatable cams 125, preferably coupled to the plate 40 to lock the spacer 20 to the plate 40 after the spacer 20 is slid onto the plate 40. Alternatively, the one or more rotatable cams 125 may act as a depth stop to prevent the plate 40 and the spacer 20 from sliding completely past one another as the spacer 20 slides onto the plate 40 to engage the projections 122 with the recesses 120, respectively. The cam 125 may be included on either or both of the upper and lower surfaces of either or both of the plate 40 and spacer 20. Preferably, for example, the plate 40 may include one or more cams 125 on the upper and lower surfaces of the plate 40, wherein the cam 125 is sized and configured to engage one or more recesses 126 formed on the upper and lower surfaces 30, 32 of the spacer 20. In use, the plate 40 and the spacer 20 may be coupled to each other by rotation of the cam 125, which may be accomplished by hand or with the benefit of a tool.

Figure 5:
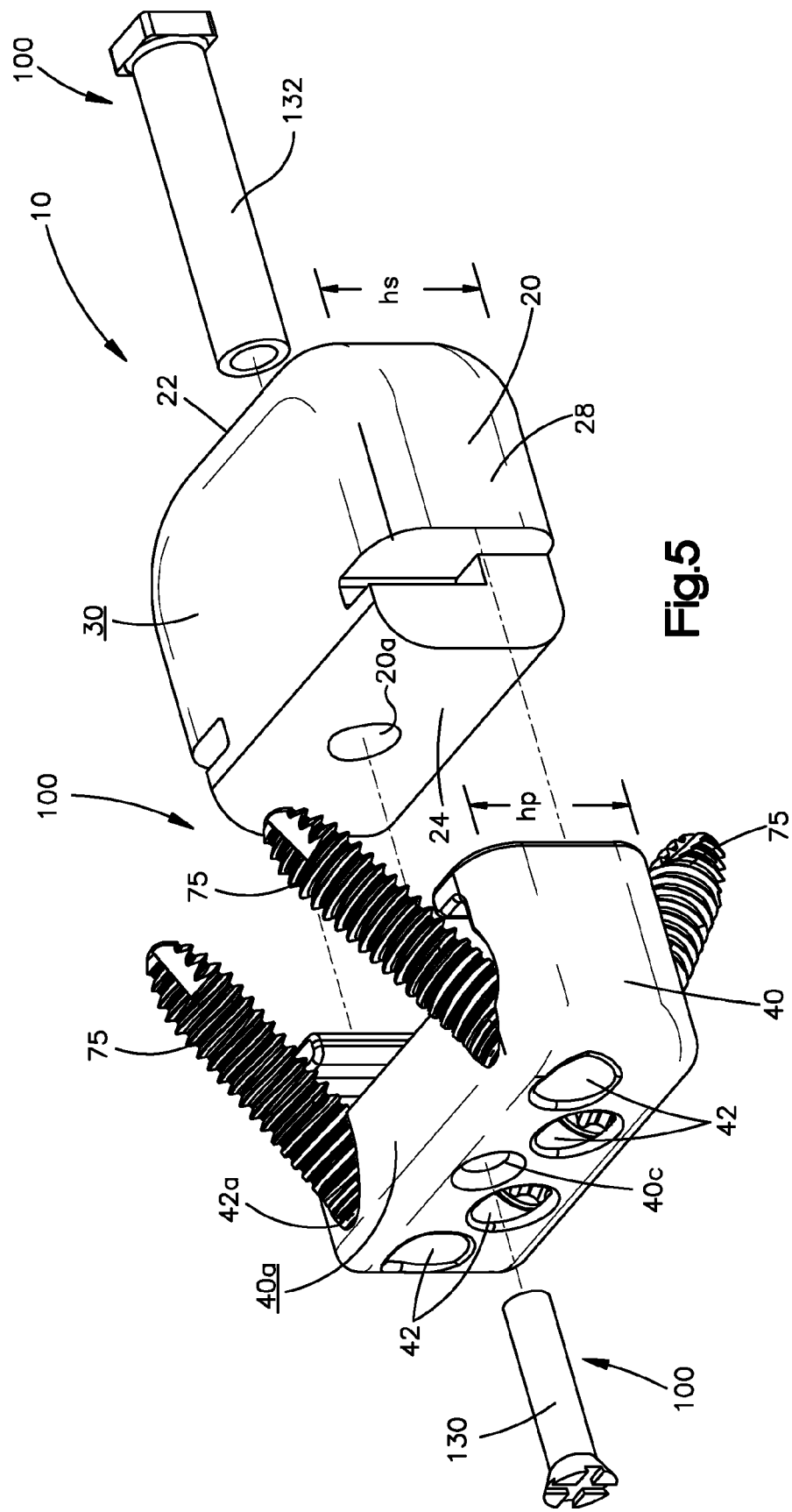
FIG. 5 illustrates a partially exploded top perspective view of an intervertebral implant in accordance with a fifth preferred embodiment of the present invention.
Figure 6:
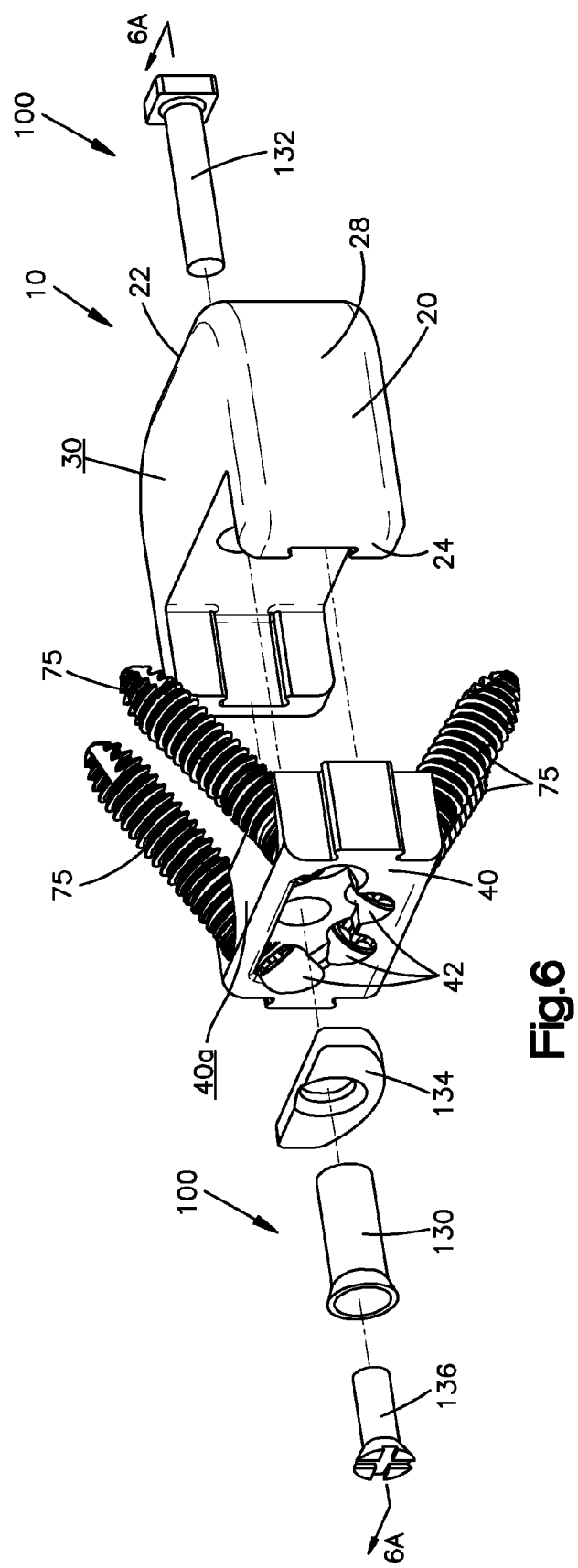
FIG. 6 illustrates a partially exploded side perspective view of an intervertebral implant in accordance with a sixth preferred embodiment of the present invention.

Referring to the fifth preferred embodiment of the intervertebral implant 10 shown in FIG. 5, the coupling mechanism 100 may include a screw 130 that is sized and configured to mate with a nut or barrel threaded pin 132 through first and second holes 20a, 40c in the spacer 20 and the plate 40, respectively. The screw 130 preferably is sized and configured to mate with the nut or barrel threaded pin 132, which may be inserted from the opposite side of the intervertebral implant 10 to secure the spacer 20 to the plate 40. In use, the screw 130 is threadably engaged to the nut or barrel threaded pin 132, thereby coupling the spacer 40 to the plate 20. As best shown in FIGS. 6 and 6A in a sixth preferred embodiment of the intervertebral implant 10, the screw 130' may be cannulated to allow inclusion and use of a blocking plate 134 and a set screw 136 to prevent "backing-out" of the fasteners 75.

Referring to the seventh preferred embodiment of the intervertebral implant 10 shown in FIG. 7, the coupling mechanism 100 may be in the form of a swag plate 140 that extends into and engages the distal end of an aperture 142 formed in the spacer 20. The plate 40 comprises two arms 144, 146 in the preferred embodiment that extend from the plate 40 into the aperture 142. In use, the arms 144, 146 may be urged together at their distal ends and inserted into the aperture 142 until the ends of the arms 144, 146 extend through the aperture 142, at which point, the arms 144, 146 are released so that the ends of the arms 144, 146, preferably protrusions formed thereon, engage the distal end of the aperture 142 of the spacer 20. The arms 144, 146 are able to flex or bend proximate their root or proximal ends such that the distal ends of the arms 144, 146 are able to slide through the aperture 142 during assembly. This embodiment enables the plate 40 to engage the spacer 20 from the inside out. In use, this embodiment enables a relatively simple assembly that permits visualization of the anterior/posterior depth of the implant 10 on an X-ray and assembly of the implant 10 in the operating room.

Referring to the eighth preferred embodiment of the intervertebral implant 10 shown in FIG. 8, the spacer 20 may have a generally rectangular or square-shape with the plate 40 mounted proximate a corner of the spacer 20. The plate 40 may be coupled to the spacer 20 by any coupling mechanisms 100 now or hereafter known for such purpose including those described herein. In use, coupling the plate 40 to a corner of the spacer 20, as opposed to one of the long ends, facilitates implanting of the intervertebral implant 10 into the disc space via an oblique angle. This embodiment is preferably used in cervical applications to limit distract the esophagus, via the approach.

Referring to the ninth preferred embodiment of the intervertebral implant 10 shown in FIG. 9, the intervertebral implant 10 includes a relatively narrow lateral footprint. In use, incorporating a narrower lateral footprint enables the intervertebral implant 10 to accommodate smaller sized patients and/or permits smaller incisions to facilitate minimally invasive techniques. The intervertebral implant 10 of the ninth preferred embodiment may be used as a strut so that the remainder of the area around the implant 10 may be packed with bone chips, putty, bone cement, etc. The intervertebral implant 10 of the ninth preferred embodiment may also enable a transpedicular posterior approach. The intervertebral implant 10 may be used for corpectomy as well as discectomy. It should be noted that any of the embodiments disclosed herein may be sized and configured to include a narrower lateral footprint.

Alternatively and/or in addition, as best shown in FIG. 10, a tenth preferred embodiment of the intervertebral implant 10 includes the plate 40 mounted to two spacers 20 such that the implant 10 is able to span one or more vertebral bodies V.

Referring to the eleventh preferred embodiment of the intervertebral implant 10 shown in FIG. 11, the plate 40 may be implanted between adjacent vertebral bodies without a spacer 20 coupled thereto so that the plate 40 may be implanted between adjacent vertebral bodies to maintain the height of the disc space while leaving the surgeon the option as to whether or not to insert an uncoupled spacer 40, bone chips, bone cement, etc. into the remaining portion of the intervertebral disc space D.

The various coupling mechanisms 100 disclosed herein may also include an adhesive bonding for additional coupling of the plate 40 to the spacer 20. That is, various methods of bonding the spacer 20 to the plate 40 may be used in connection with the various coupling mechanisms 100 disclosed herein. These methods, may include, but are not limited to, chemical bonding or process, ultrasound, ultraviolet light, adhesives, bone welding, clamping etc. These methods may be used in addition, or instead of other coupling mechanisms 100.

Furthermore, referring to a twelfth preferred embodiment of the intervertebral implant 10 shown in FIG. 12, the intervertebral implant 10 may be constructed completely of a monolithic material and has angled bores and fasteners 75. The implant 10 and the fasteners 75 are preferably constructed of the same material, which may be, but is not limited to PEEK, titanium, a resorbable polymer, or magnesium. The implant 10 of the twelfth preferred embodiment may be constructed exclusively of a resorbable material that completely resorbes into a patient's body following implantation. Preferably, the intervertebral implant 10 of the twelfth preferred embodiment is made from an allograft material. The intervertebral implant 10 of the twelfth preferred embodiment may be constructed such that the fasteners 75 are formed from synthetic bone material, which may be inserted and thereafter welded to the adjacent vertebral bodies V to thereby couple the intervertebral implant 10 to the adjacent vertebral bodies V. Alternatively, the synthetic bone material fasteners 75 may be constructed without threads in the form of pins. Such synthetic bone fasteners 75 may be non-threaded or include, for example, push-out resistant Christmas tree threads or other types of threads. Incorporation of synthetic bone material fasteners 75 facilitates manufacturing of the intervertebral implant 10 by eliminating metallic components from the implant 10, thereby enabling constructions using exclusively allograft or resorbable materials.

Alternatively, the intervertebral implant 10 of the twelfth preferred embodiment may incorporate a plate 40 coupled to the spacer 20 and welded to the synthetic bone material fasteners 75 by, for example, ultrasound, thereby eliminating the need for any mechanical locking mechanism when the fasteners are mounted in the through holes 42 in an implanted position. In use, manufacturing the spacer 20 from an allograft or resorbable material and incorporating synthetic bone material fasteners 75 results in only the plate remaining within the patient, if any component of the implant 10 remains within the patient, due to the materials resorbing into the patient's body. It should be noted, however, that it is envisioned that synthetic bone material fasteners 75, which may be welded in-situ to the adjacent vertebral bodies V, may be used in connection with any of the intervertebral implants 10 now or hereafter known including any of the various embodiments of the implant 10 described herein.

The intervertebral implants 10 of each of the twelve preferred embodiments are generally sized and configured for anterior insertion, although different configurations may be possible for lateral, antero-lateral or posterior approaches. In addition to the features described, the intervertebral implant 10 may include threaded holes, slots or channels to mate with instruments to facilitate manipulation and insertion.

Although the present invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art. For example, the present invention may be employed in different sections of the spinal column, including, but not limited to, the cervical area.

The invention claimed is:

1. A low profile intervertebral implant sized and configured to be implanted between adjacent upper and lower vertebral bodies, the implant comprising:
    a spacer having a first insertion end, a second end opposite the first insertion end, a first lateral surface, a second lateral surface, an upper surface for contacting the upper vertebral body when in an implanted configuration, a lower surface for contacting the lower vertebral body when in the implanted configuration; and
    a plate coupled to the second end of the spacer, the plate including a plurality of through holes for receiving a plurality of bone screws for securing the implant to the adjacent vertebral bodies, the plate having a height $H_p$ while the second end of the spacer has a height $H_s$, the height $H_p$ of the plate being equal to or less than the height of the spacer $H_s$ so that the plate does not increase a height profile of the spacer; and
    wherein the plate is coupled to the spacer via first and second arms extending from the plate, the first arm extending along the first lateral surface of the spacer, having a first end, and bending around the first insertion end of the spacer and the second arm extending along the second lateral surface of the spacer, having a second end, and bending around the first insertion end of the spacer, wherein the first and second ends of the first and second arms define a gap therebetween.

2. The implant of claim 1, wherein the plate is formed from a first material and the spacer is formed from a second material, the first material being different from the second material.

3. The implant of claim 2, wherein the first material is a metallic material and the second material is non-metallic.

4. The implant of claim 1, wherein the first and second arms are in the form of a split ring.

5. The implant of claim 4, wherein the first and second arms defining the split ring are deformable around the spacer.

6. The implant of claim 4, wherein the first and second arms defining the split ring are selectively interconnected with one another so that the first and second arms may be placed around the spacer and then tightened to operatively couple the plate to the spacer.

7. The implant of claim 1, wherein the gap is located along the first insertion end of the spacer.

8. The implant of claim 1, wherein the gap is located proximate a corner of the spacer, and the corner is located at an intersection of the first insertion end and the first lateral surface or an intersection of the first insertion end and the second lateral surface.

9. The implant of claim 1, wherein the spacer is a single spacer.

10. The implant of claim 1, wherein the spacer comprises a coplanar upper surface and a coplanar lower surface.

11. The implant of claim 10, wherein the upper surface of the spacer or the lower surface of the spacer is tapered.

12. The implant of claim 1, wherein the plurality of through holes are angled with respect to the upper surface of the spacer and the lower surface of the spacer.

13. The implant of claim 1, wherein the spacer is formed of an allograft.

14. The implant of claim 1, wherein the upper and lower surfaces of the spacer include a series of teeth.

15. A low profile intervertebral implant sized and configured to be implanted between adjacent upper and lower vertebral bodies, the implant comprising:
    a spacer having a first insertion end, a second end opposite the first insertion end, a first lateral surface, a second lateral surface, an upper surface for contacting the upper vertebral body when in an implanted configuration, a lower surface for contacting the lower vertebral body when in the implanted configuration; and
    a plate coupled to the second end of the spacer, the plate including a plurality of through holes for receiving a plurality of bone screws for securing the implant to the adjacent vertebral bodies, the plate having a height $H_p$ while the second end of the spacer has a height $H_s$, the height $H_p$ of the plate being equal to or less than the height of the spacer $H_s$ so that the plate does not increase a height profile of the spacer; and
    wherein the plate is coupled to the spacer via first and second arms extending from the plate with a gap therebetween, the first arm extending along the first lateral surface of the spacer and bending around the first insertion end of the spacer and the second arm extending along the second lateral surface of the spacer and bending around the first insertion end of the spacer.

* * * * *

UNITED STATES PATENT AND TRADEMARK OFFICE
CERTIFICATE OF CORRECTION

PATENT NO. : 8,540,774 B2
APPLICATION NO. : 12/743098
DATED : September 24, 2013
INVENTOR(S) : Kueenzi et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 327 days.

Signed and Sealed this
Fifteenth Day of September, 2015

Michelle K. Lee
*Director of the United States Patent and Trademark Office*